(12) United States Patent
Jensen et al.

(10) Patent No.: US 10,758,306 B2
(45) Date of Patent: *Sep. 1, 2020

(54) FREQUENCY IDENTIFICATION FOR MICROWAVE ABLATION PROBES

(71) Applicant: Covidien LP, Mansfield, MA (US)

(72) Inventors: Jeffrey L. Jensen, Boulder, CO (US); Joseph D. Brannan, Lyons, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/102,260

(22) Filed: Aug. 13, 2018

(65) Prior Publication Data

US 2018/0344398 A1 Dec. 6, 2018

Related U.S. Application Data

(63) Continuation of application No. 12/423,609, filed on Apr. 14, 2009, now Pat. No. 10,045,819.

(51) Int. Cl.
*A61B 18/18* (2006.01)
*A61B 90/98* (2016.01)
*A61B 18/00* (2006.01)

(52) U.S. Cl.
CPC .......... *A61B 18/18* (2013.01); *A61B 18/1815* (2013.01); *A61B 90/98* (2016.02); *A61B 2018/00196* (2013.01); *A61B 2018/00988* (2013.01); *A61B 2018/1869* (2013.01)

(58) Field of Classification Search
CPC ............ A61B 18/18; A61B 90/98; A61B 2018/00196; A61B 2018/00988; A61B 2018/1869
See application file for complete search history.

(56) References Cited

U.S. PATENT DOCUMENTS

| | | |
|---|---|---|
| 3,631,363 A | 12/1971 | Miller |
| 4,397,313 A | 8/1983 | Vaguine |
| 4,462,412 A | 7/1984 | Turner |
| 4,572,190 A | 2/1986 | Azam et al. |

(Continued)

FOREIGN PATENT DOCUMENTS

| | | |
|---|---|---|
| DE | 390937 C | 3/1924 |
| DE | 1099658 B | 2/1961 |

(Continued)

OTHER PUBLICATIONS

Anonymous. (2001) Disposable Chiba Biopsy Needles and Trays, Biopsy and Special Purpose Needles Cook Diagnostic and Interventional Products Catalog (products list), 4 pages.

(Continued)

*Primary Examiner* — Lauren P Farrar

(57) ABSTRACT

A microwave ablation system is disclosed. The system includes a microwave antenna assembly that includes an identification device configured to store an optimal frequency of the microwave antenna assembly. The system also includes a generator configured to couple to the microwave antenna assembly and to output microwave energy at an operational frequency. The generator is further configured to read the optimal frequency from the identification device and to configure the operational frequency to substantially match the optimal frequency.

15 Claims, 3 Drawing Sheets

(56) References Cited

U.S. PATENT DOCUMENTS

| | | | |
|---|---|---|---|
| 4,798,215 A | 1/1989 | Turner | |
| 5,097,844 A | 3/1992 | Turner | |
| 5,383,874 A | 1/1995 | Jackson et al. | |
| 5,400,267 A | 3/1995 | Denen et al. | |
| 5,413,573 A | 5/1995 | Koivukangas | |
| 5,417,210 A | 5/1995 | Funda et al. | |
| 5,425,704 A | 6/1995 | Sakurai et al. | |
| 5,540,683 A | 7/1996 | Ichikawa et al. | |
| 5,651,780 A | 7/1997 | Jackson et al. | |
| 5,693,042 A | 12/1997 | Boiarski et al. | |
| 5,792,138 A | 8/1998 | Shipp | |
| 6,014,581 A | 1/2000 | Whayne et al. | |
| 6,031,375 A | 2/2000 | Atalar et al. | |
| 6,055,458 A | 4/2000 | Cochran et al. | |
| 6,068,627 A | 5/2000 | Orszulak et al. | |
| 6,074,386 A | 6/2000 | Goble et al. | |
| 6,090,123 A | 7/2000 | Culp et al. | |
| 6,142,992 A | 11/2000 | Cheng et al. | |
| 6,165,173 A * | 12/2000 | Kamdar | A61B 18/1206 606/34 |
| 6,214,003 B1 | 4/2001 | Morgan et al. | |
| 6,235,020 B1 | 5/2001 | Cheng et al. | |
| 6,296,636 B1 | 10/2001 | Cheng et al. | |
| 6,375,606 B1 | 4/2002 | Garibaldi et al. | |
| 6,402,743 B1 | 6/2002 | Orszulak et al. | |
| 6,464,689 B1 | 10/2002 | Qin et al. | |
| 6,464,696 B1 | 10/2002 | Oyama et al. | |
| 6,603,994 B2 | 8/2003 | Wallace et al. | |
| 6,623,423 B2 | 9/2003 | Sakurai et al. | |
| 6,663,623 B1 | 12/2003 | Oyama et al. | |
| 6,666,860 B1 | 12/2003 | Takahashi | |
| 6,685,701 B2 | 2/2004 | Orszulak et al. | |
| 6,725,080 B2 | 4/2004 | Melkent et al. | |
| 6,733,495 B1 | 5/2004 | Bek et al. | |
| 6,740,085 B2 | 5/2004 | Hareyama et al. | |
| 6,783,523 B2 | 8/2004 | Qin et al. | |
| 6,843,789 B2 | 1/2005 | Goble | |
| 6,893,435 B2 | 5/2005 | Goble | |
| 6,994,704 B2 | 2/2006 | Qin et al. | |
| 7,044,949 B2 | 5/2006 | Orszulak et al. | |
| 7,063,692 B2 | 6/2006 | Sakurai et al. | |
| 7,169,144 B2 | 1/2007 | Hoey et al. | |
| 7,214,224 B2 | 5/2007 | Goble | |
| 7,306,592 B2 | 12/2007 | Morgan et al. | |
| 7,439,736 B2 | 10/2008 | Meaney et al. | |
| 7,467,015 B2 | 12/2008 | van der Weide | |
| 7,565,207 B2 | 7/2009 | Turner et al. | |
| 2002/0022836 A1 | 2/2002 | Goble et al. | |
| 2003/0139741 A1 | 7/2003 | Goble et al. | |
| 2003/0199856 A1 | 10/2003 | Hill et al. | |
| 2004/0016246 A1 | 1/2004 | Furukawa et al. | |
| 2004/0044339 A1 | 3/2004 | Beller et al. | |
| 2004/0097805 A1 | 5/2004 | Verard et al. | |
| 2004/0133189 A1 | 7/2004 | Sakurai | |
| 2004/0172016 A1 | 9/2004 | Bek et al. | |
| 2004/0242992 A1 | 12/2004 | Hareyama | |
| 2004/0267297 A1 | 12/2004 | Malackowski | |
| 2005/0004634 A1 | 1/2005 | Ricart et al. | |
| 2005/0228370 A1 | 10/2005 | Sterzer et al. | |
| 2006/0030914 A1 | 2/2006 | Eggers et al. | |
| 2006/0106375 A1 | 5/2006 | Werneth et al. | |
| 2006/0200120 A1 | 9/2006 | DiCarlo et al. | |
| 2006/0224152 A1 | 10/2006 | Behnke et al. | |
| 2007/0032784 A1 * | 2/2007 | Gliklich | A61B 8/4411 606/27 |
| 2007/0100405 A1 | 5/2007 | Thompson et al. | |
| 2007/0219548 A1 * | 9/2007 | Carr | A61B 18/18 606/33 |
| 2008/0004615 A1 | 1/2008 | Woloszko et al. | |
| 2009/0030437 A1 * | 1/2009 | Houser | A61L 2/07 606/169 |
| 2010/0082022 A1 | 4/2010 | Haley | |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0246350 A1 | 11/1987 |
| EP | 0481685 A1 | 4/1992 |
| EP | 0521264 A2 | 1/1993 |
| EP | 0556705 A1 | 8/1993 |
| EP | 0558429 A1 | 9/1993 |
| EP | 0572131 A1 | 12/1993 |
| EP | 0541930 B1 | 3/1998 |
| EP | 0836868 A2 | 4/1998 |
| EP | 1278007 A1 | 1/2003 |
| EP | 1159926 A2 | 3/2003 |
| EP | 1810627 A1 | 7/2007 |
| FR | 179 607 | 11/1906 |
| FR | 1 275 415 | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 | 12/1994 |
| JP | 07265328 | 10/1995 |
| JP | 08056955 | 3/1996 |
| JP | 08252263 A | 10/1996 |
| JP | 09010223 | 1/1997 |
| JP | 11244298 | 9/1999 |
| JP | 2000342599 A | 12/2000 |
| JP | 2000350732 A | 12/2000 |
| JP | 2001008944 | 1/2001 |
| JP | 2001029356 | 2/2001 |
| JP | 2001128990 A | 5/2001 |
| SU | 166452 | 1/1965 |
| SU | 401367 A1 | 10/1973 |

(56) References Cited

FOREIGN PATENT DOCUMENTS

| | | | |
|---|---|---|---|
| SU | 727201 | A2 | 4/1980 |
| WO | 9724073 | A1 | 7/1997 |
| WO | 9741924 | A1 | 11/1997 |
| WO | 9743971 | A2 | 11/1997 |
| WO | 0048672 | A1 | 8/2000 |
| WO | 0051513 | A1 | 9/2000 |
| WO | 0101847 | A1 | 1/2001 |
| WO | 0174252 | A2 | 10/2001 |
| WO | 0245790 | A2 | 6/2002 |
| WO | 2002061880 | A2 | 8/2002 |
| WO | 2004112628 | A1 | 12/2004 |
| WO | 2005016119 | A2 | 2/2005 |
| WO | 2008071914 | A2 | 6/2008 |

OTHER PUBLICATIONS

Anonymous. (1987) Homer Mammalok. TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management. Feb. 2003.
B. Levy M.D.. "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology. vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1, (Jul. 1991) pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al.. "Antennas for Medical Applications", Antenna Handbook: Theory Application and Design, p. 24-40. Van Nostrand Reinhold, 1988 New York, V.T. Lo, S.W. Lee.
Carbonell et al., "Comparison of the Gyms PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure. TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52. No. 3.
Chou, C.K., (1995) "Radiofrequency Hyperthermia in Cancer Therapy," Chapter 94 1n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone", Neurosurgery 15: (1984) pp. 945-950.
Cosman et al., "Methods of Making Nervous System Lesions", in William RH, Rengachary SS (eds): Neurosurgery, New York: McGraw-Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.
Dulemba et al. "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence", Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure. TM. Vessel Sealing System: A Case Report" Innovations That Work, Feb. 2002.
Ian D. McRury et al., the Effect of Ablation Sequence and Duration on Lesion Shape Using Rapidly Pulsed Radiofrequency Energy Through Electrodes, Feb. 2000, Springer Netherlands. vol. 4; No. 1. pp. 307-320.
Johnson et al. "Evaluation of a Bipolar Electrothermal Vessel Sealing Device in Hemorrhoidectomy" Sales/Product Literature; Jan. 2004.
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole, M.D., et al., "Biopsy Needle Characteristics Assessed in the Laboratory", Radiology 148: 659-662, Sep. 1983.
Joseph Ortenberg, " LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al. "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May-Jun. 1982.

(56) References Cited

OTHER PUBLICATIONS

Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 2006.
European Search Report EP 05022350.2 dated Jan. 30, 2006.
European Search Report EP 05023017.6 dated Feb. 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.

(56) References Cited

OTHER PUBLICATIONS

European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
McLellan et al., "Vessel Sealing for Hemostasis During Pelvic Surgery" Int'l Federation of Gynecology and Obstetrics FIGO World Congress 2000, Washington, DC.
MDtech product literature (Mar. 2000) I'D Wire: product description, 1 page.
MDtech product literature (Dec. 1999) "FlexStrand": product description, 1 page.
Medtrex Brochure "The O.R. Pro 300" 1 page; Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform": Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" the American Journal of Surgery, vol. 181, No. 3, Apr. 2001 pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure. "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite Element Codes to Model Electrical Heating and Non Linear Thermal Transport in Biological Media", Proc. ASME HTD-355, 131 (1997).
Urologix, Inc.—Medical Professionals: Targis.TM. Technology (Date Unknown). "Overcoming the Challenge" located at: <http://www.urologix.com/medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—COA-COMP" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
International Search Report PCT/US99/24869 dated Feb. 11, 2000.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.

(56) References Cited

OTHER PUBLICATIONS

European Search Report EP 08012829.1 dated Oct. 29, 2008.
European Search Report EP 08019920.1 dated Mar. 27, 2009.
European Search Report EP 081699718 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.

\* cited by examiner

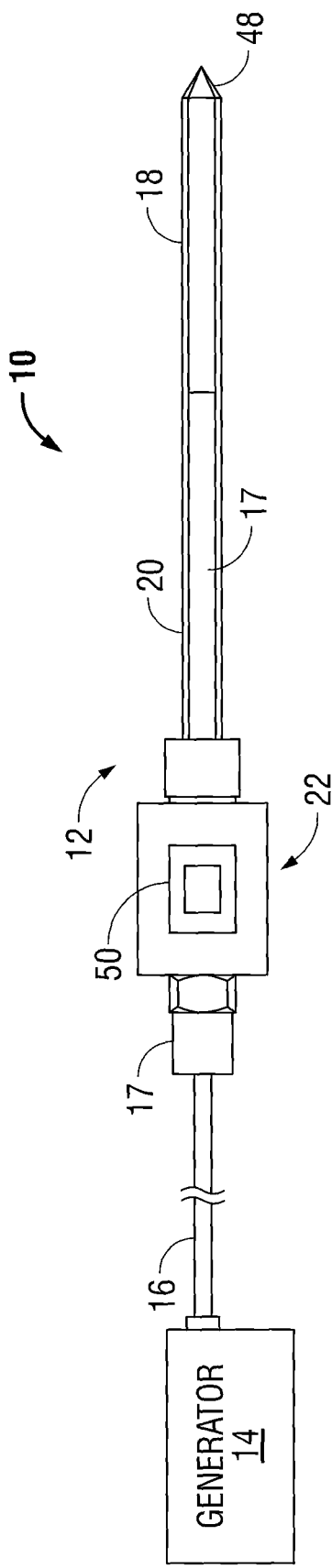
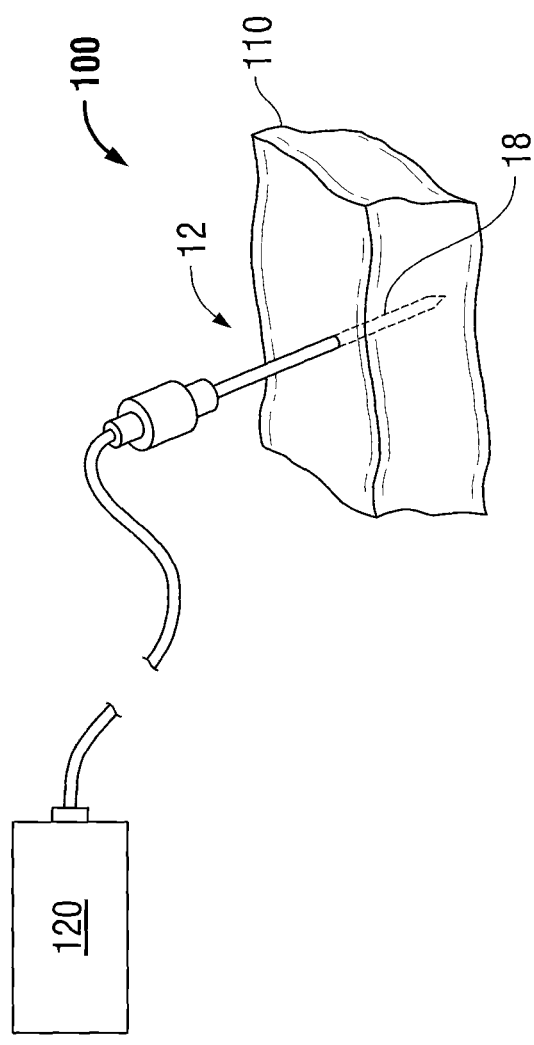

FREQUENCY IDENTIFICATION FOR MICROWAVE ABLATION PROBES

CROSS-REFERENCE TO RELATED APPLICATIONS

The present application is a continuation of U.S. patent application Ser. No. 12/423,609, filed on Apr. 14, 2009, the entire disclosure of which is incorporated by reference herein.

BACKGROUND

1. Technical Field

The present disclosure relates generally to microwave antennas used in tissue ablation procedures. More particularly, the present disclosure is directed to optimal frequency identification for microwave ablation antennas.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

Due to manufacturing tolerance limitations, each microwave antenna assembly has a unique optimal operational frequency.

SUMMARY

The present disclosure provides for a system and method that allow for identification of specific operational frequency of each microwave antenna assembly. The operational frequency may be encoded as a resistance value or in memory available for measurement or reading by a microwave ablation generator. The generator may then be configured to substantially match the operational frequency to the optimal frequency of each antenna assembly. Matching the output frequency to optimal frequency maximizes antenna assembly's efficiency and energy delivery to the target tissue, thereby improving ablation size and reducing the ablation time. Utilizing optimal frequency for each antenna assembly also reduces reflected energy from the assembly back to the generator, which in turn, reduces heating of the entire system. Further, the system and method of the present disclosure provide for an additional quality check of the antenna assembly during the manufacturing process, allowing for discarding of any antenna assemblies whose optimal frequency falls outside an expected deviation from a desired operational range. In addition, the system and method according to the present disclosure allow for use of antenna assemblies with a wider range of manufacturing tolerances, since the operational frequency may be used to tune the generator to a desired frequency that best matches the determined frequency of the antenna assembly. Without this tuning capability and using a fixed frequency generator, the optimal operating frequency for a given antenna might be outside the usable frequency range of the generator, which results in inefficient application of microwave energy.

According to one embodiment of the present disclosure, a microwave ablation system is provided. The system includes a microwave antenna assembly that includes an identification device configured to store an optimal frequency of the microwave antenna assembly. The system also includes a generator configured to couple to the microwave antenna assembly and to output microwave energy at an operational frequency. The generator is further configured to read the optimal frequency from the identification device and to configure the operational frequency to substantially match the optimal frequency.

According to another embodiment of the present disclosure, a microwave ablation antenna assembly is provided. The antenna assembly includes an identification device configured to store an optimal frequency of the microwave antenna assembly and a radiating section coupled to a hub having a cable adapted to couple the microwave antenna assembly to a generator configured to output microwave energy at an operational frequency. The generator is further configured to read the optimal frequency from the identification device and to configure the operational frequency to substantially match the optimal frequency.

A method for microwave ablation is also contemplated by the present disclosure. The method includes the steps of: immersing at least a portion of a microwave antenna assembly in a model tissue, determining optimal frequency of the microwave antenna assembly within the model tissue and recording the optimal frequency in an identification device associated with the microwave antenna assembly.

BRIEF DESCRIPTION OF THE DRAWINGS

The above and other aspects, features, and advantages of the present disclosure will become more apparent in light of the following detailed description when taken in conjunction with the accompanying drawings in which:

FIG. 1 is a schematic diagram of a microwave ablation system according to an embodiment of the present disclosure;

FIG. 2 is a schematic diagram of a system for determining optimal operational frequency of a microwave antenna assembly according to an embodiment of the present disclosure;

DETAILED DESCRIPTION

Figure 3:
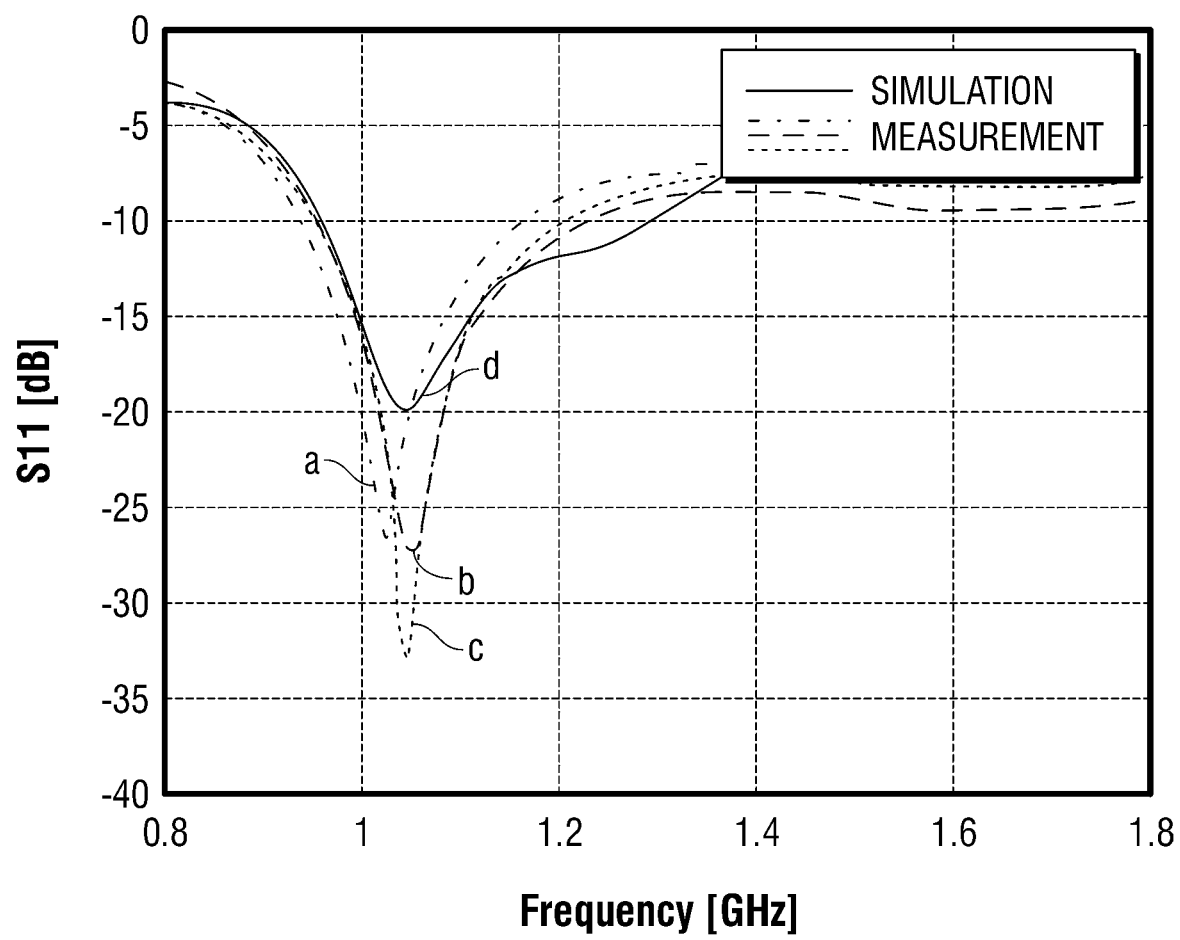
FIG. 3 is a plot of scattering parameter measurements for a plurality of microwave antenna assemblies.

Particular embodiments of the present disclosure will be described herein below with reference to the accompanying drawings. In the following description, well-known functions or constructions are not described in detail to avoid obscuring the present disclosure in unnecessary detail.

Microwave antenna assemblies are typically resonant structures, which operate most efficiently at a particular frequency. In other words, due to manufacturing tolerance limitations, each microwave antenna assembly has a unique optimal operational frequency. The present disclosure provides for a system and method for determining the operational frequency of the microwave antenna assembly and providing the optimal frequency to a microwave generator, which then adjusts output of the microwave energy accordingly to substantially match the optimal frequency.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 10,000 MHz. In the illustrated embodiment, the antenna assembly 12 includes a radiating section 18 connected by feedline 20 (or shaft) to the cable 16, the radiating section 18 having a tip 48 at its distal end. More specifically, the feedline 20 is connected to a hub 22 which is connected to the cable 16 through a cable connector 17. The hub 22 may have a variety of suitable shapes, e.g., cylindrical, rectangular, etc. In one embodiment, the feedline 20 may be formed from a coaxial, semi-rigid or flexible cable having a wire with a 0.047" outer diameter rated for 50 Ohms.

FIG. 2 illustrates a system 100 for determining optimal operational frequency of the microwave antenna assembly 12. The microwave antenna assembly 12 is inserted into a tissue model 110 at least to fully submerge the radiating section 18 therein. The tissue model 110 may be any suitable material that models targeted tissue of interest. In particular, the material may closely approximate complex dielectric properties of targeted tissue. The material may be actual tissue, e.g., liver tissue, muscle tissue, etc. or synthetic variant thereof (e.g., ceramic, tissue phantom, etc.). Tissue phantoms may be manufactured from various types of gels, e.g., hydrogel.

The system 100 also includes a network analyzer 120 configured to measure scattering parameters of the microwave antenna assembly 12. The network analyzer 120 acts as a microwave generator and supplies a simulation pulse to the microwave antenna assembly 12, to provide a simulation of operating parameters reflective of actual application of microwave energy to tissue. During simulated treatment, the scattering of the microwave energy is measured by the network analyzer 120. In one embodiment, the network analyzer 120 measures a reflected signal of the measurement pulse, which is reflective of the scattering parameters of the microwave antenna assembly 12, such as optimal frequency, electrical length, phase, and the like. Measurement of scattering parameters may be accomplished during production of the antenna assembly 12 (e.g., testing the response of the antenna assembly 12 in the model tissue 110 after assembly thereof).

As discussed above, individual microwave antenna assemblies 12 display varying scattering parameters, such as optimal operating frequencies. FIG. 3 shows a plot of scattering parameter measurements for three different microwave antenna assemblies 12, marked as a, b and c, respectively, and a simulation plot d. The plots illustrate resonant performance of each of the microwave antenna assemblies 12 in terms of decibels (shown from 0 to −40 dB to illustrate a reflected signal) of the reflected signal across a 1 GHz frequency range from about 0.8 GHz to about 1.8 GHz. A simulated graph d is also shown, which illustrates expected optimal frequency response from the microwave antenna assembly 12 at about 1.04 GHz with a signal strength response of about −20 dB. In comparison, the graphs a, b and c illustrate that the actual signal and frequency responses vary for each of the microwave antenna assemblies 12. In particular, the graph a shows an optimal frequency response at about 1.04 GHz, the graphs b and c show optimal frequency responses at about 1.05 GHz, whereas graph b has a signal response similar to the graph a at about −27 dB and the graph c has a signal response similar to the graph c at about −33 dB.

As shown in FIG. 3, each microwave antenna assembly 12 has a specific operational frequency. To achieve maximum efficiency from the microwave antenna assembly 12, it is desirable to supply microwave energy thereto at the predetermined operational frequency as determined by the network analyzer 120. Conventionally, the microwave generator 14 supplies the energy at a stated frequency designated for an entire type (e.g., model) of the microwave antenna assembly without accounting for frequency variations between each specific microwave antenna assembly 12. The present disclosure provides for a system and method to provide the predetermined optimal frequency of the microwave antenna 12 to the generator 14, such that the generator 14 tunes the operational output frequency to the optimal frequency.

With reference again to FIG. 1, the antenna assembly 12 includes an identification device 50 disposed thereon for encoding the optimal frequency. More specifically, during production of the microwave assembly 12, the frequency is determined as discussed above with respect to FIG. 3. The determined optimal frequency is then encoded in the identification device 50. During operation, the identification device 50 is read by the microwave generator 14 to determine the optimal frequency, and the generator 14 then adjusts the output to suit that frequency. In one embodiment, the identification device 50 may also include other information, such as model number, energy delivery characteristics and physical characteristics (e.g., length of the radiating section 18) of the microwave antenna assembly 12. This information may also be used by the generator 14 to adjust the output.

In one embodiment, the identification device 50 may be a storage device such as a microcontroller, microprocessor, non-volatile memory (e.g., EPROM), radio frequency identification tags. Information can be transmitted to the generator 14 via a variety of communication protocols (e.g., wired or wireless) between the microwave assembly 12 and the generator 14. In this embodiment, the optimal frequency is stored in the storage device which is extracted by the generator 14 through a communication port (e.g., serial or parallel data bus).

In another embodiment, the identification device 50 may be any suitable identifier, such as optical, displacement, magnetic or electrical (e.g., conductance, resistance, capacitance, impedance) component. In this embodiment, the optimal frequency is encoded as a resistance, capacitance, etc. The generator 14 supplies an electrical current signal through the identification device 50, which allows the generator 14 to measure the resistance or another electrical property of the identification device 50 and then determine the optimal frequency that corresponds to the measured resistance. The generator 14 may also include a storage device having a lookup table or a microprocessor adapted to process the resistance value to determine the corresponding optimal frequency.

In a further embodiment, the identification device 50 may be a barcode or another type of optically encoded storage device. The optimal frequency may be read by scanning the barcode using various types of barcode readers. The barcode may store the actual optimal frequency or a code associated therewith, which when read by the generator 14 may be then determined to correspond to the frequency.

Once the generator 14 determines the optimal frequency from the identification device 50, the output of the microwave energy to the antenna assembly 12 is tuned to the optimal frequency. The generator 14 is a tunable microwave generator that may operate at a variable output frequency. The generator 14 may include a phase lock loop (PLL) to set an operational frequency to the optimal frequency. The PLL may be implemented as a digital or analog circuit. The PLL of the generator 14 controls the operational frequency throughout the procedure, maintaining the operational frequency within the desired range of the operational frequency.

Figure 4:
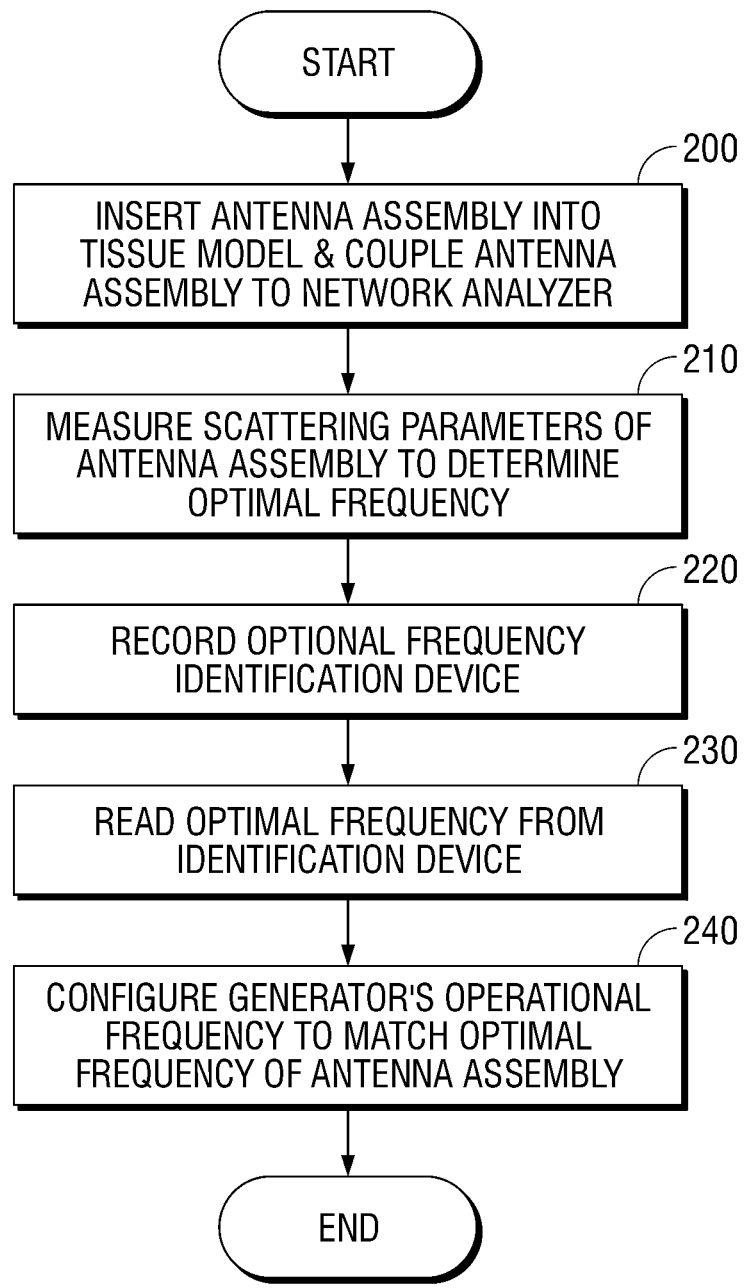
FIG. 4 is a flow diagram of a method for determining optimal operational frequency of a microwave antenna assembly according to an embodiment of the present disclosure.

FIG. 4 illustrates a flow diagram of a method for determining optimal operational frequency of a microwave antenna assembly 12. In step 200, the antenna assembly 12 is inserted into model tissue 110 and is also coupled to the network analyzer 120. In step 210, the network analyzer 120 provides one or more test pulses to the antenna assembly 12 to determine the optimal frequency thereof. In step 220, the optimal frequency is recoded in the identification device 50 of the antenna assembly 12. During use of the antenna assembly 12, in step 230, the optimal frequency is read from the identification device 50 by the generator 14. In step 240, the generator 14 configures the operational frequency thereof to match the optimal frequency of the antenna assembly 12 as read from the identification device 50.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A microwave ablation system, comprising:
at least one microwave antenna assembly including an identification device storing an optimal frequency for operating the at least one microwave antenna assembly; and
a generator configured to couple to the at least one microwave antenna assembly and to output microwave energy at an operational frequency thereto, the generator further configured to read the optimal frequency from the identification device and to configure the operational frequency to substantially match the optimal frequency.

2. The system according to claim 1, wherein the identification device is selected from the group consisting of a microcontroller, a microprocessor, a non-volatile memory, a radio frequency identification tag, a resistor and a capacitor.

3. The system according to claim 1, wherein the optimal frequency of the at least one microwave antenna assembly is determined while immersing at least a portion of the at least one microwave antenna assembly in a model tissue and applying at least one simulation pulse.

4. The system according to claim 3, wherein the optimal frequency of the at least one microwave antenna assembly is determined by measuring at least one scattering parameter of the at least one microwave antenna assembly in response to the at least one simulation pulse.

5. The system according to claim 1, wherein the generator includes a phase lock loop adapted to maintain the operational frequency to substantially match the optimal frequency.

6. The system according to claim 1, wherein the at least one microwave antenna assembly includes a hub configured to couple the at least one microwave antenna to the generator, and the identification device is formed on the hub.

7. A microwave ablation system, comprising:
a microwave ablation antenna assembly including an identification device storing data including a predetermined optimal frequency for operating the microwave ablation antenna assembly; and
a generator configured to:
couple to the microwave ablation antenna assembly;
output microwave energy at an operational frequency;
read the predetermined optimal frequency from the identification device; and
set the operational frequency to the predetermined optimal frequency.

8. The microwave ablation system according to claim 7, wherein the microwave ablation antenna assembly further includes a hub and the identification device is disposed on the hub.

9. The microwave ablation system according to claim 8, wherein the microwave ablation antenna assembly further includes:
a radiating section coupled to the hub; and
a cable adapted to couple the hub to the generator.

10. The microwave ablation system according to claim 7, wherein the generator includes a phase lock loop circuit configured to tune the microwave energy to the predetermined optimal frequency.

11. The microwave ablation system according to claim 7, wherein the identification device is selected from the group consisting of a non-volatile memory, a radio frequency identification tag, a resistor, and a capacitor.

12. The microwave ablation system according to claim 7, wherein the operational frequency of the microwave ablation antenna assembly is determined while immersing at least a portion of the microwave ablation antenna assembly in a model tissue.

13. The microwave ablation system according to claim 12, wherein the operational frequency of the microwave ablation antenna assembly is determined by measuring at least one scattering parameter of the microwave ablation antenna assembly in response to at least one simulation pulse applied to the microwave ablation antenna assembly.

14. A microwave ablation system, comprising:
a microwave antenna configured to deliver microwave energy to tissue, the microwave antenna including a hub;
a generator coupleable to the hub of the microwave antenna for delivering the microwave energy to the microwave antenna; and an identification device formed on the hub of the microwave antenna and storing an optimal frequency for operating the microwave antenna to deliver the microwave energy to the tissue.

15. The microwave ablation system according to claim 14, wherein the generator is configured to set an operational frequency of the microwave antenna to the optimal frequency stored in the identification device.

* * * * *